United States Patent
Masutani et al.

(10) Patent No.: US 9,943,501 B2
(45) Date of Patent: Apr. 17, 2018

(54) PPAR-GAMMA ACTIVATOR

(71) Applicant: KOJUN JAPAN CO., LTD., Osaka-shi, Osaka (JP)

(72) Inventors: Bumbu Masutani, Osaka (JP); Yoshio Tsujino, Kobe (JP); Jiyeong An, Kyoto (JP); Atsushi Yamatsu, Kyoto (JP); Yusuke Yamashita, Kyoto (JP); Seiyu Harada, Kyoto (JP)

(73) Assignee: KOJUN JAPAN CO., LTD., Osaka (JP)

( * ) Notice: Subject to any disclaimer, the term of this patent is extended or adjusted under 35 U.S.C. 154(b) by 0 days.

(21) Appl. No.: 15/306,887

(22) PCT Filed: Jul. 3, 2015

(86) PCT No.: PCT/JP2015/069281
§ 371 (c)(1),
(2) Date: Oct. 26, 2016

(87) PCT Pub. No.: WO2016/006548
PCT Pub. Date: Jan. 14, 2016

(65) Prior Publication Data
US 2017/0105965 A1    Apr. 20, 2017

(30) Foreign Application Priority Data

Jul. 11, 2014  (JP) ................. 2014-143247
Mar. 13, 2015  (JP) ................. 2015-051006

(51) Int. Cl.
*A61K 31/365* (2006.01)

(52) U.S. Cl.
CPC .................. *A61K 31/365* (2013.01)

(58) Field of Classification Search
CPC ................................................ A61K 31/365
USPC ....................................................... 514/473
See application file for complete search history.

(56) References Cited

FOREIGN PATENT DOCUMENTS

| JP | 2005-168387 A | 6/2005 |
| JP | 2009-249322 A | 10/2009 |
| JP | 2011-51952 A | 3/2011 |
| WO | 2013/187381 A1 | 12/2013 |

OTHER PUBLICATIONS

Simone et al.,"Toward the Discovery of New Agents Able to Inhibit the Expression of Microsomal Prostaglandin E Synthase-1 Enzyme as Promising Tools in Drug Development", Chem. Biol. Drug Des., (2010), vol. 76, pp. 17-24, (Cited in ISR) (7 pages).
International Search Report dated Aug. 18, 2015, issued in counterpart International Application No. PCT/JP2015/069281 (2 pages).
Mallory, F.B. et al, "Small-Ring Compounds: XXX. Reactions of Phenylcyclobutadienoquinone with Methanol", Journal of the American Chemical Society, 1961, vol. 83, pp. 393-397; cited in Extended (supplementary) European Search Report dated Dec. 1, 2017.
Mehta, G. et al, "An Expeditious Synthesis of 4-Aryl-Gamma-Butyrolactones, -Furan-2(5H)-ones and -5-Alkoxyfuran-2(5H)-ones via Heck-reaction of Arenediazonium Salts with 2,5-Dihydrofuran", Tetrahedron Letters, 1996, vol. 37, No. 47, pp. 8625-8626; cited in Extended (supplementary) European Search Report dated Dec. 1, 2017.
Parker, A.N. et al, "Synthesis of 4-Benzyl-3-Phenylbutenolide Natural Products", Tetrahedron Letters, 2013, vol. 54, pp. 5322-5324; cited in Extended (supplementary) European Search Report dated Dec. 1, 2017.
Bourguignon, J.J. et al, "Lactone Chemistry. Synthesis of Beta-Substituted, Gamma-Functionalized Butanolides and Butenolides and Succinaldehydic Acids from Glyoxylic Acid", J. Org. Chem, 1981, vol. 46, No. 24, pp. 4889-4894; cited in Extended (supplementary) European Search Report dated Dec. 1, 2017.
Extended (supplementary) European Search Report dated Dec. 1, 2017, issued in counterpart European Application No. 15819179.1. (8 pages).

*Primary Examiner* — Kristin Vajda
(74) *Attorney, Agent, or Firm* — Westerman, Hattori, Daniels & Adrian, LLP

(57) ABSTRACT

The present invention provides A PPARγ activator comprising a butenolide compound represented by the formula (1) or a pharmaceutically acceptable salt thereof:

[Formula 1]

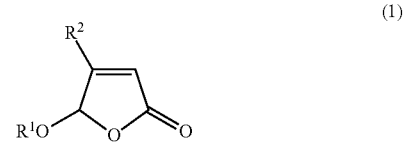

(1)

wherein $R^1$ represents a hydrogen atom, a phosphate group, a fatty acid group, an alkyl group having 1 to 4 carbon atoms and optionally having a substituent or a sugar residue optionally having a substituent, and $R^2$ represents a phenyl group, a methylphenyl group, a dimethylphenyl group, an ethylphenyl group, a benzyl group, a methylbenzyl group, a dimethylbenzyl group, an ethylbenzyl group, a phenethyl group, a methylphenethyl group, a dimethylphenethyl group, or an ethylphenethyl group.

5 Claims, 10 Drawing Sheets

[Figure 1]
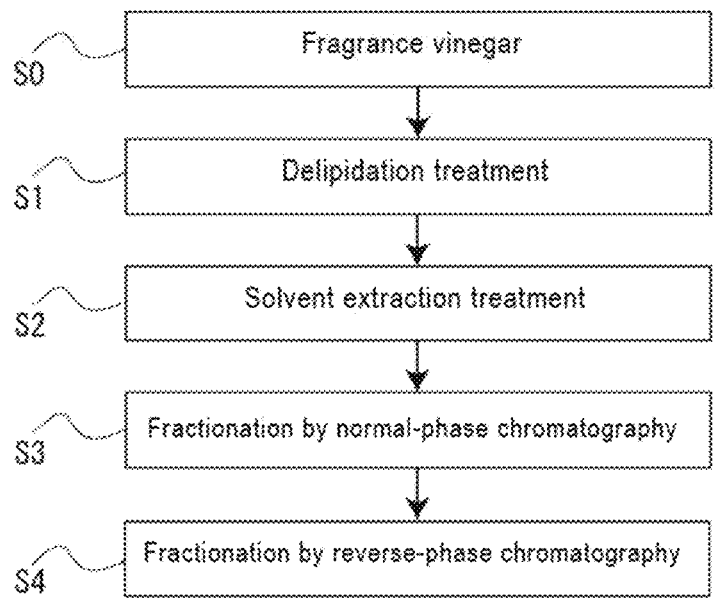
[Figure 2]
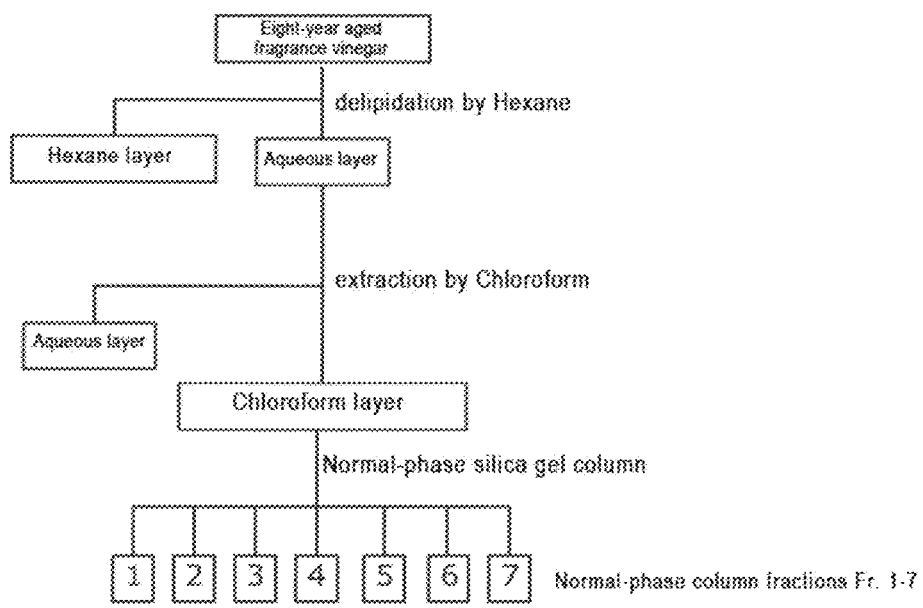

[Figure 3]
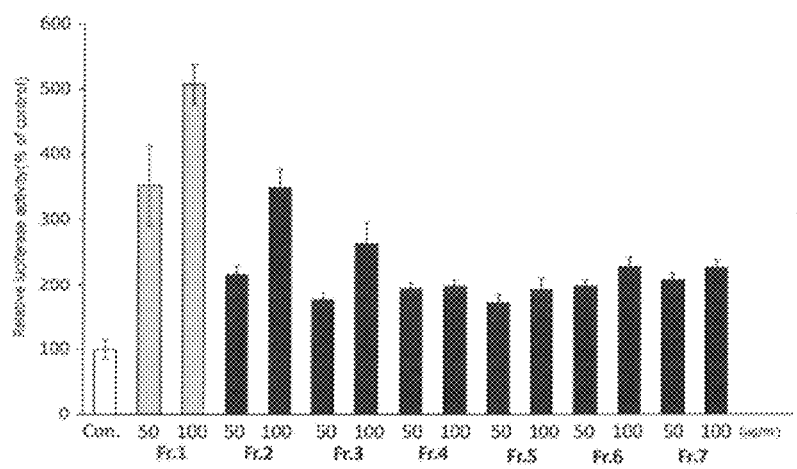
[Figure 4]
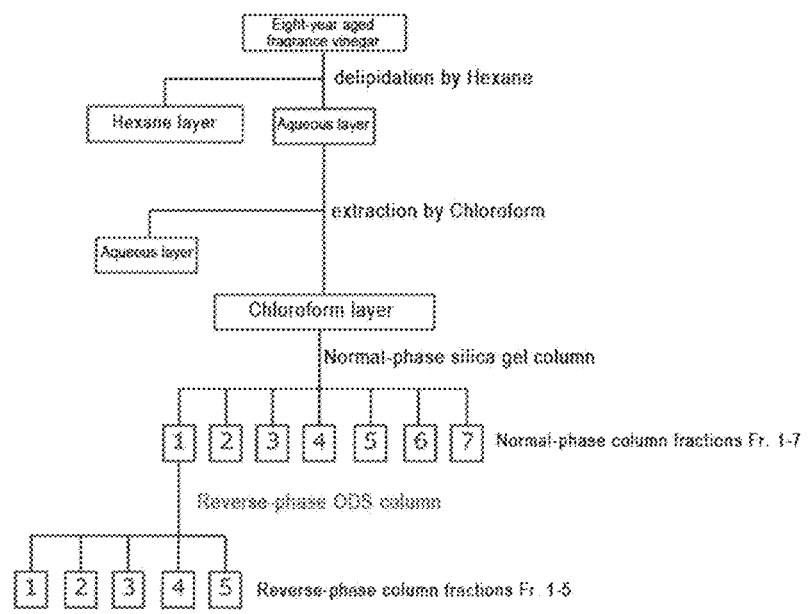

[Figure 5]
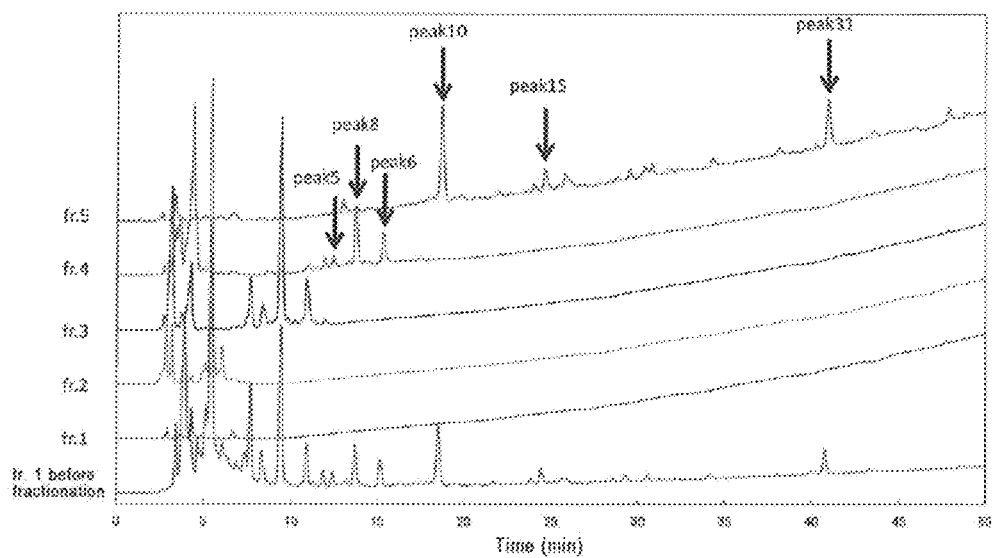
[Figure 6]
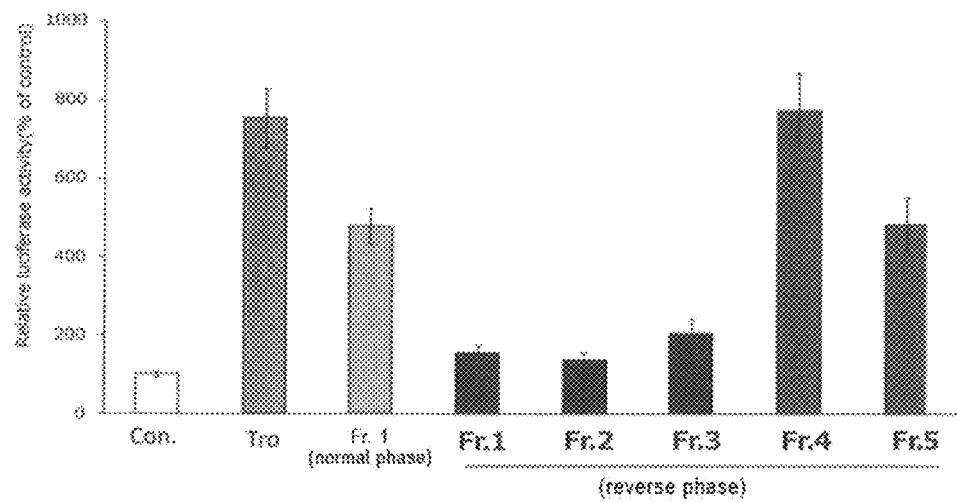

[Figure 7]
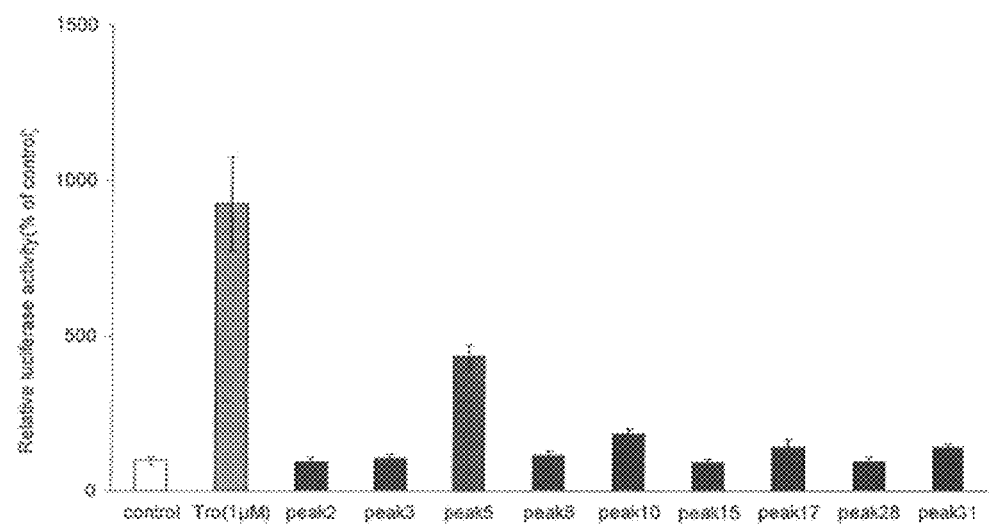
[Figure 8]
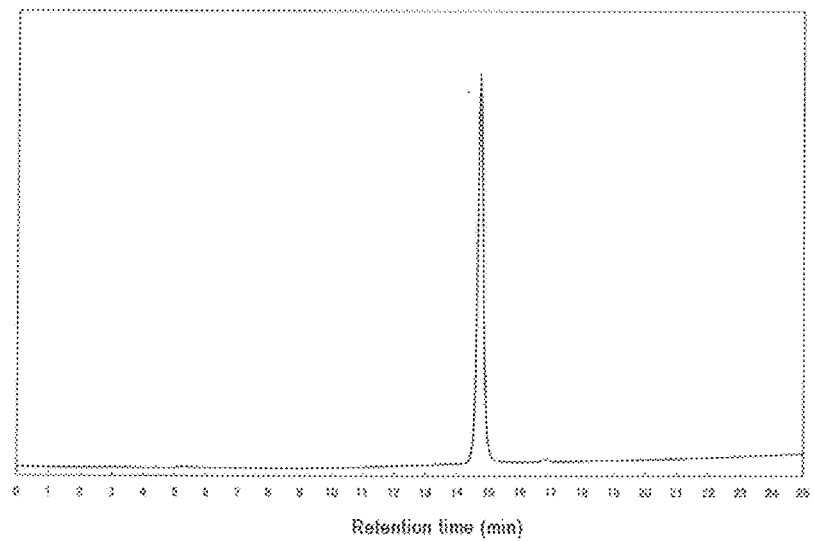

[Figure 9]
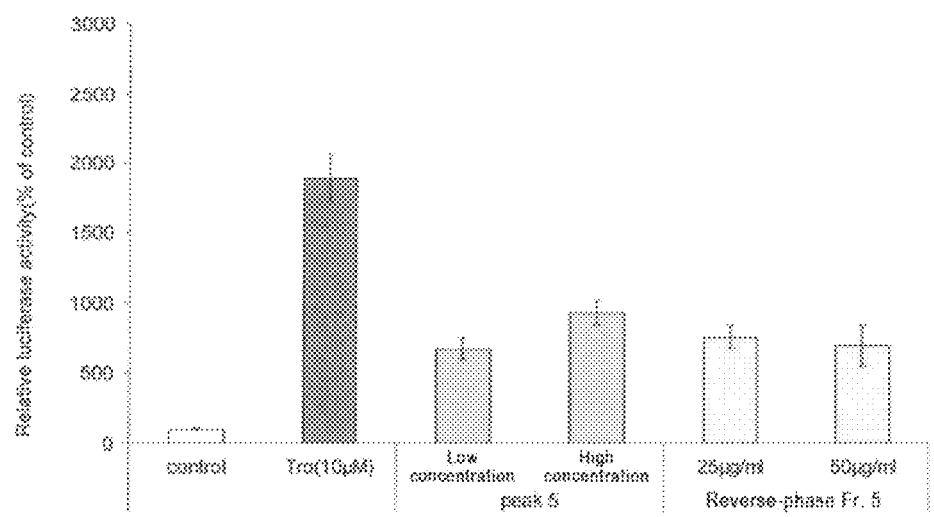
[Figure 10]
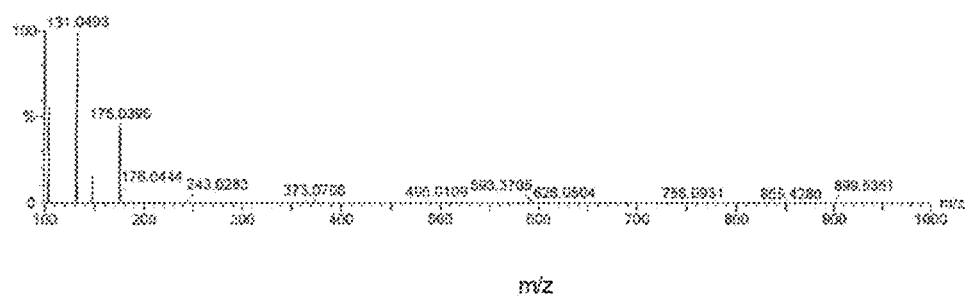

[Figure 11]
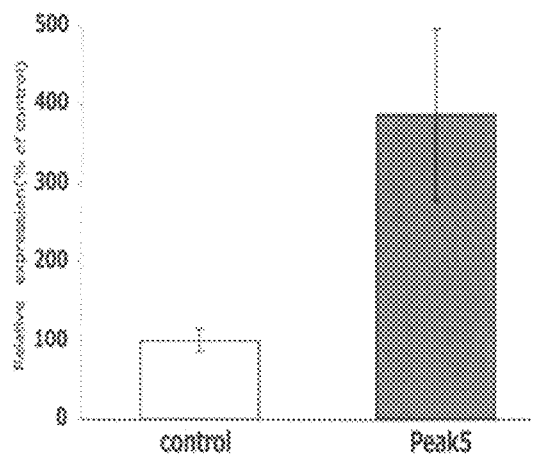
[Figure 12]
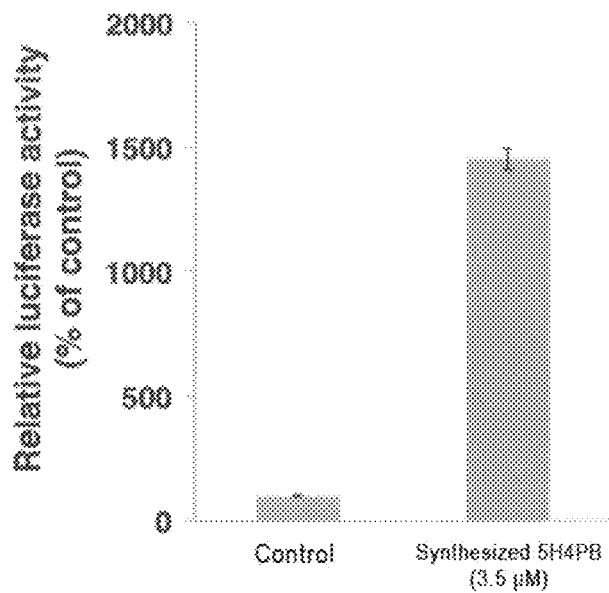

[Figure 13]
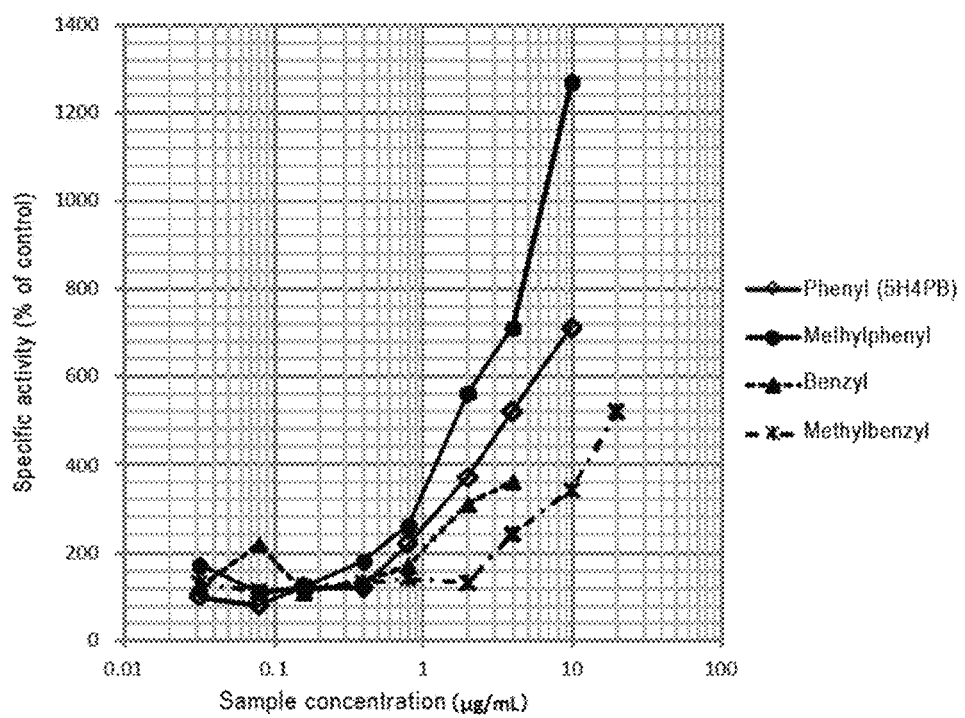

[Figure 14]
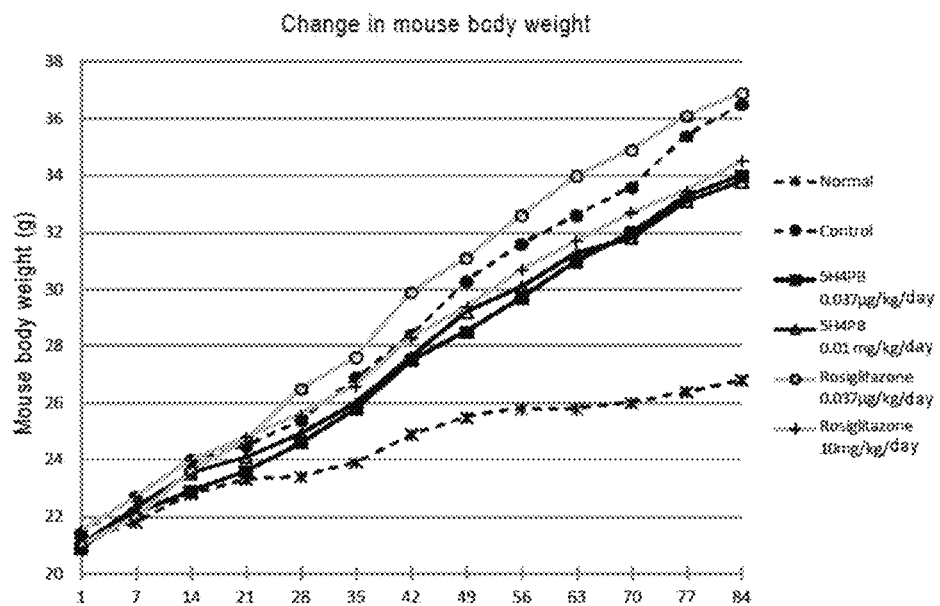
[Figure 15]
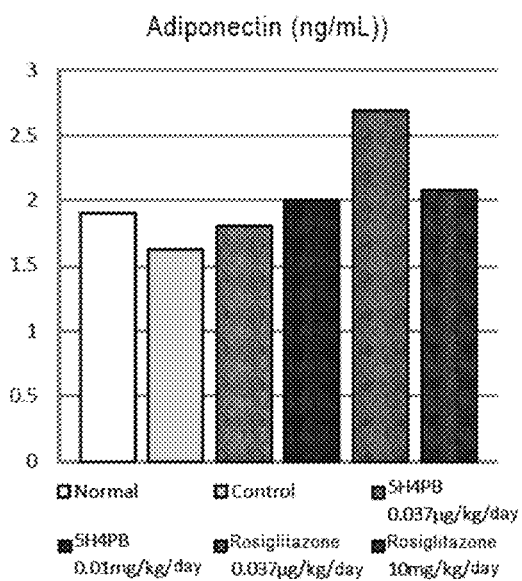

[Figure 16]
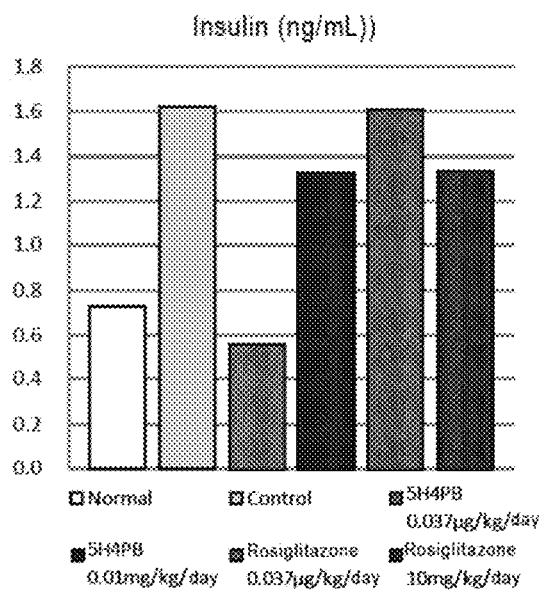
[Figure 17]
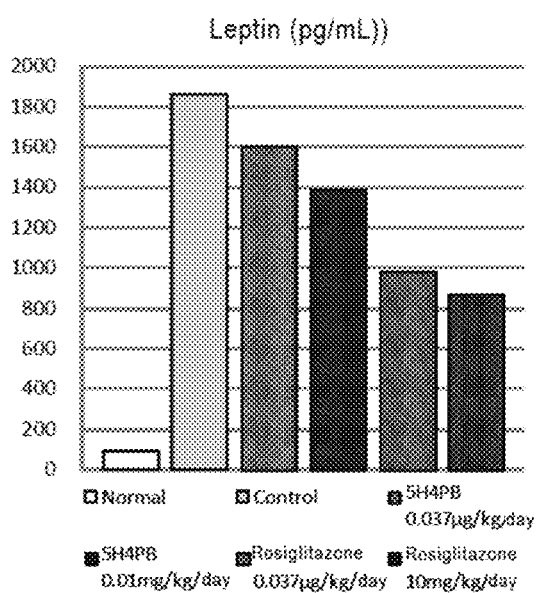

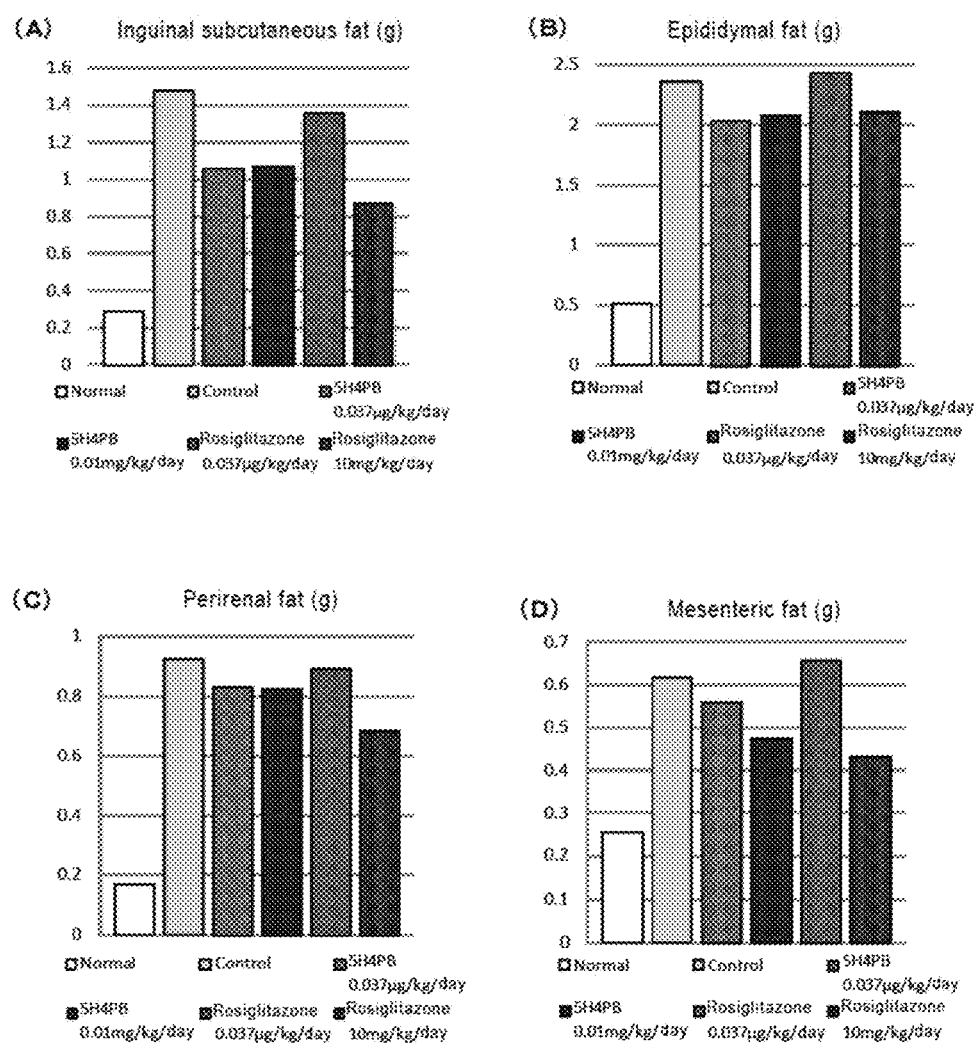
[Figure 10]

PPAR-GAMMA ACTIVATOR

TECHNICAL FIELD

The present invention relates to a PPARγ activator that can be used for a lipid metabolism activator, an antidiabetic agent, or the prevention or amelioration, etc., of obesity, lifestyle-related diseases, or the like.

BACKGROUND ART

Fragrance vinegars (aromatic vinegars) are fermented foods that are typically produced by the fermentation of glutinous rice followed by aging for a long period, and have been used as vinegar seasonings in China from a long time ago. The fragrance vinegars have also become increasingly popular in Japan in recent years as health foods that help maintain or promote health, because of their higher contents of organic compounds such as amino acids than those of rice vinegars, which are vinegars generally used in Japan.

For example, the present inventors disclose, in Patent Literature 1, a peroxisome proliferator-activated receptor α activator and a peroxisome proliferator-activated receptor γ activator each containing a lower alkanol extract of fragrance vinegar as an active ingredient. This literature states that the lower alkanol extract of a fragrance vinegar exhibits the peroxisome proliferator-activated receptor (PPAR) α-activating effect of improving sugar metabolism by participating in the stimulation of fatty acid oxidation and mediating effects on serum lipids as well as the PPARγ-activating effect of bringing about, for example, decreases in blood glucose level and lipids in blood by participating in the differentiation of fat cells.

CITATION LIST

Patent Literature

[Patent Literature 1] Japanese Patent Laid-Open No. 2009-249322

SUMMARY OF INVENTION

Technical Problem

Since the PPAR activators disclosed in Patent Literature 1, however, were extracts obtained by extraction using a lower alkanol from fragrance vinegar, the PPARγ-activating effects of these extracts were generally validated in an experimental system under adjusted reaction conditions as compared with in vivo experiments. These PPARγ-activating effects were confirmed when a cell culture solution was supplemented with each lower alkanol extract of a fragrance vinegar at a ratio as high as 1.0% (i.e., 10000 ppm). Accordingly, this lower alkanol extract of fragrance vinegar needs to be added or ingested in a large amount for use as a PPARγ activator.

Also, the lower alkanol extract of fragrance vinegar disclosed in Patent Literature 1 is a mixture containing a plurality of components. A specific active ingredient as a PPAR activator has not been shown therein.

Thus, an object of the present invention is to identify an active ingredient having an excellent PPAR-activating effect contained in fragrance vinegars and to provide a PPAR activator containing the active ingredient.

Solution to Problem

To attain the object, the present inventors have subjected fragrance vinegars to various fractionation treatments and studied the obtained fractions. As a result, the present inventors have found a butenolide compound having a PPAR-activating effect. Specifically, the PPARγ activator of the present invention comprises a butenolide compound represented by the formula (1) or a pharmaceutically acceptable salt thereof:

[Formula 1]

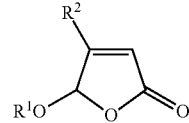

(1)

wherein $R^1$ represents a hydrogen atom, a phosphate group, a fatty acid group, an alkyl group having 1 to 4 carbon atoms and optionally having a substituent, or a sugar residue optionally having a substituent, and $R^2$ represents a phenyl group, a methylphenyl group, a dimethylphenyl group, an ethylphenyl group, a benzyl group, a methylbenzyl group, a dimethylbenzyl group, an ethylbenzyl group, a phenethyl group, a methylphenethyl group, a dimethylphenethyl group, or an ethylphenethyl group.

This butenolide compound has PPARγ ligand activity and has the effect of activating PPARγ. This butenolide compound also has the effects of converting white fat cells to brown fat cells and activating lipid metabolism. This butenolide compound is further effective for the prevention, amelioration, or treatment, etc., of a pathological condition, a symptom, or a disease involving PPARγ, such as diabetes mellitus, insulin resistance, hyperlipidemia, hypertension, arteriosclerosis visceral fat obesity, subcutaneous fat accumulation, body weight gain, leptin resistance, fatty liver, or lifestyle-related diseases.

In the PPARγ activator of the present invention, preferably, in the aforementioned formula (1), $R^1$ is a hydrogen atom, a phosphate group, or a sugar residue optionally having a substituent, and $R^2$ is a phenyl group, a 4-methylphenyl group, a benzyl group, or a 4-methylbenzyl group. A butenolide compound is thereby selected as a preferable PPARγ activator having water-soluble properties.

The pharmaceutical drug of the present invention is a pharmaceutical drug for the prevention or treatment of at least one disease selected from the group consisting of diabetes mellitus, insulin resistance, obesity, body weight gain, visceral fat accumulation, subcutaneous fat accumulation, leptin resistance, abnormal lipid metabolism, hyperlipidemia, arteriosclerosis, and metabolic syndrome, the pharmaceutical drug comprising the aforementioned PPARγ activator. Preferred use of the PPARγ activator consisting of the aforementioned butenolide compound is thereby selected.

The supplement of the present invention is a supplement for the prevention or amelioration of at least one disease selected from the group consisting of diabetes mellitus, insulin resistance, obesity, body weight gain, visceral fat accumulation, subcutaneous fat accumulation, leptin resistance, abnormal lipid metabolism, hyperlipidemia, arteriosclerosis, and metabolic syndrome, the supplement comprising the aforementioned PPARγ activator. Preferred use of the PPARγ activator consisting of the aforementioned butenolide compound is thereby selected.

The composition of the present invention for the treatment, prevention, inhibition, or amelioration of a pathological condition, a symptom, or a disease involving PPARγ comprises a butenolide compound represented by the formula (2) or a pharmaceutically acceptable salt thereof as an active ingredient:

[Formula 2]

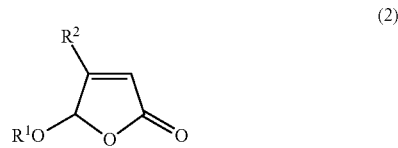

(2)

wherein $R^1$ represents a hydrogen atom, a phosphate group, a fatty acid group, an alkyl group having 1 to 4 carbon atoms and optionally having a substituent, or a sugar residue optionally having a substituent, and $R^2$ represents a phenyl group, a methylphenyl group, a dimethylphenyl group, an ethylphenyl group, a benzyl group, a methylbenzyl group, a dimethylbenzyl group, an ethylbenzyl group, a phenethyl group, a methylphenethyl group, a dimethylphenethyl group, or an ethylphenethyl group.

PPARγ is a factor involved mainly in sugar or lipid metabolism and is involved in metabolic syndrome, metabolic diseases, body weight gain, visceral fat accumulation, subcutaneous fat accumulation, obesity, diabetes mellitus, insulin resistance, hypertension, arteriosclerosis, hyperlipidemia, inflammatory diseases, and proliferative diseases including malignant tumors. The butenolide compound mentioned above has PPARγ ligand activity and has the effect of activating PPARγ. The butenolide compound is therefore effectively used for the prevention, amelioration, inhibition, or treatment of a pathological condition, a symptom, or a disease involving PPARγ.

The pathological condition, the symptom, or the disease involving PPARγ is preferably one or more pathological conditions, symptoms, or diseases selected from the group consisting of diabetes mellitus, insulin resistance, obesity, body weight gain, visceral fat accumulation, subcutaneous fat accumulation, leptin resistance, abnormal lipid metabolism, hyperlipidemia, arteriosclerosis, and metabolic syndrome. Particularly preferred use of the aforementioned butenolide compound is thereby selected. This butenolide compound has the effects of converting white fat cells to brown fat cells, promoting heat production by use of lipids, and activating lipid metabolism and further has a body weight gain inhibitory effect, a visceral fat accumulation inhibitory effect, a subcutaneous fat accumulation inhibitory effect, an adiponectin-enhancing effect, an insulin secretion inhibitory effect, and a leptin secretion inhibitory effect, etc. Hence, the butenolide compound can treat, prevent, inhibit, or ameliorate these pathological conditions, symptoms, or diseases involving PPARγ.

Advantageous Effects of Invention

According to the present invention, a butenolide compound having a high PPARγ-activating effect can be obtained. This butenolide compound has the effects of converting white fat cells to brown fat cells and activating lipid metabolism and further has a body weight gain inhibitory effect, a visceral fat accumulation inhibitory effect, an adiponectin-enhancing effect, an insulin secretion inhibitory effect, and a leptin secretion inhibitory effect, etc. Hence, the butenolide compound can be used for the treatment, prevention, inhibition, or amelioration of a pathological condition, a symptom, or a disease involving PPARγ, such as insulin resistance, diabetes mellitus, body weight gain, obesity, hyperlipidemia, hypertension, arteriosclerosis, visceral fat accumulation, subcutaneous fat accumulation, fatty liver, or metabolic syndrome. Thus, the obtained butenolide compound helps prevent or ameliorate these pathological conditions, etc., and is widely applicable to foods, supplements, drugs, or the like.

BRIEF DESCRIPTION OF DRAWINGS

FIG. 1 is a flowchart schematically illustrating a method for producing a butenolide compound serving as an active ingredient in the PPARγ activator of the present invention, from a fragrance vinegar.

FIG. 2 is a flowchart schematically illustrating a method for preparing normal-phase column fractions from fragrance vinegar in Example 1.

FIG. 3 is a graph showing the PPARγ ligand activity of the normal-phase column fractions in Example 1.

FIG. 4 is a flowchart schematically illustrating a method for preparing reverse-phase column fractions in Example 2.

FIG. 5 is a chromatogram showing results of HPLC analysis on the reverse-phase column fractions (fr. 1 to 5) obtained in Example 2 and the normal-phase column fraction (fr. 1 before fractionation) obtained in Example 1. The abscissa depicts retention time (min).

FIG. 6 is a graph showing the PPARγ ligand activity of the reverse-phase column fractions in Example 2.

FIG. 7 is a graph showing the PPARγ ligand activity of peak fractions obtained in Example 3.

FIG. 8 is a chromatogram showing results of HPLC analysis on peak 5 among the peak fractions obtained in Example 3. The ordinate depicts detection intensity. The abscissa depicts retention time (min).

FIG. 9 is a graph showing the PPARγ ligand activity of the fraction of peak 5 in Example 3 and the reverse-phase column fraction of Fr. 5 obtained in Example 2.

FIG. 10 is a chart showing results of LC/MS on the fraction of peak 5 in Example 4. The ordinate depicts detection intensity. The abscissa depicts m/z values.

FIG. 11 is a graph showing results about the expression level of UCP-1 gene in Example 5.

FIG. 12 is a graph showing the PPARγ ligand activity of synthesized 5-hydroxy-4-phenylbutenolide in Example 7.

FIG. 13 is a graph showing the PPARγ ligand activity of butenolide compounds in Example 8.

FIG. 14 is a graph showing the body weight gain inhibitory effect of 5-hydroxy-4-phenylbutenolide administered to mice in Example 9.

FIG. 15 is a graph showing the amount of adiponectin contained in mouse blood in Example 10.

FIG. 16 is a graph showing the amount of insulin contained in mouse blood in Example 11.

FIG. 17 is a graph showing the amount of leptin contained in mouse blood in Example 12.

FIG. 18 is a graph showing the subcutaneous fat and visceral fat accumulation inhibitory effects of 5-hydroxy-4-phenylbutenolide administered to mice in Example 13.

DESCRIPTION OF EMBODIMENTS

Hereinafter, the present invention will be described in detail. The PPARγ activator of the present invention comprises a butenolide compound represented by the aforementioned formula (1) as an active ingredient. In this formula (1), the atom represented by $R^1$ is preferably a hydrogen atom. Examples of the molecule represented by $R^1$ include a phosphate group, a fatty acid group, an alkyl group having 1 to 4 carbon atoms and optionally having a substituent, and a sugar residue optionally having a substituent. Examples of the fatty acid group include lauric acid, myristic acid, palmitic acid, margaric acid, and stearic acid. Examples of the alkyl group having 1 to 4 carbon atoms include a methyl group, an ethyl group, various propyl groups, and various butyl groups. The phosphate group or a glycoside derived from the sugar residue is preferred from the viewpoint of ex vivo stability and in vivo absorbability. The sugar is not particularly limited, and, for example, various glucoses, various galactoses, or various mannoses are used. Particularly, a glucose is preferably used as the sugar forming a glycoside.

$R^2$ is preferably a phenyl group, a methylphenyl group, a dimethylphenyl group, an ethylphenyl group, a benzyl group, a methylbenzyl group, a dimethylbenzyl group, an ethylbenzyl group, a phenethyl group, a methylphenethyl group, a dimethylphenethyl group, or an ethylphenethyl group. Particularly, a phenyl group, a 4-methylphenyl group, a benzyl group, or a 4-methylbenzyl group is preferably used from the viewpoint of effects.

Of the compounds represented by this formula (1), examples of the compound particularly preferred in terms of pharmacological activity can include 5-hydroxy-4-phenyl-butenolide represented by the formula (3) given below and 5-hydroxy-4-(4-methylphenyl)butenolide represented by the formula (4) given below as well as 5-hydroxy-4-(4-methylbenzyl)butenolide and 5-hydroxy-4-benzylbutenolide. As mentioned later, 5-hydroxy-4-phenylbutenolide or 5-hydroxy-4-(4-methylphenyl)butenolide, which has been found as a PPARγ activator in fragrance vinegar, is particularly preferred.

[Formula 3]

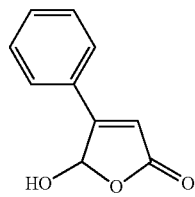

(3)

[Formula 4]

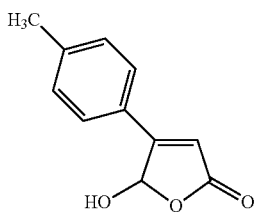

(4)

The butenolide compound represented by the formula (3), i.e., 5-hydroxy-4-phenylbutenolide, can be obtained by extraction from fragrance vinegar, which is a fermented food. The method for obtaining this butenolide compound from a fragrance vinegar is not particularly limited and, as an example, comprises, as schematically shown in the flowchart of FIG. 1, fragrance vinegar (a step of preparing a fragrance vinegar) S0, delipidation treatment step S1 of removing lipid components contained in the fragrance vinegar, solvent extraction treatment step S2 of extracting the component of interest using a solvent, fractionation step S3 by normal-phase chromatography, and fractionation step S4 by reverse-phase chromatography.

This fragrance vinegar S0 is prepared by: adding koji (rice malt) to glutinous rice for alcohol fermentation; adding rice husk to the resulting product for acetic acid fermentation; carrying out extraction by the addition of water; and aging the extract for a given period.

The delipidation treatment S1 shown in FIG. 1 is carried out for the purpose of removing redundant lipid components contained in the fragrance vinegar S0. Since the delipidation treatment of the fragrance vinegar S0 removes the redundant lipid components contained in the fragrance vinegar, the butenolide compound represented by the formula (3) can be effectively extracted in the subsequent solvent extraction treatment S2 or the fractionation steps S3 and S4. Specifically, this treatment can be carried out, but not particularly limited to, by: adding an organic solvent to the fragrance vinegar S0; well stirring the mixture so that the redundant lipid components are transferred to an organic solvent phase; then separating an aqueous phase from the organic solvent phase using a centrifuge; and recovering the aqueous phase. This operation is preferably carried out several times. The organic solvent can be any solvent having a delipidating effect. For example, a petroleum-based organic solvent or an alcohol is preferably used, and n-hexane is particularly preferably used. The amount of the organic solvent used is preferably on the order of 10% by weight to 1000% by weight of the fragrance vinegar, most preferably on the order of half to twice the amount of the fragrance vinegar.

Next, the solvent extraction treatment S2 shown in FIG. 1 involves adding a solvent to the fragrance vinegar that has undergone the delipidation treatment so that the butenolide compound of interest is transferred to the added solvent. An organic solvent is preferably used as the solvent. For example, an alkanol such as n-butanol or ethanol, ethyl acetate, butylene glycol, or chloroform can be used, though the solvent is not particularly limited thereto. Such a solvent extraction treatment S2 is not limited to a single treatment, and the extraction treatment may be carried out several times using the same solvent or plural types of solvent extraction treatments may be carried out in combination.

All extraction treatment using chloroform as the organic solvent will be described as one example of the aforementioned solvent extraction treatment S2. This chloroform extraction treatment involves adding chloroform to the delipidated fragrance vinegar so that the butenolide compound as the component of interest is efficiently transferred to a chloroform phase. Specifically, this treatment is carried out, for example, by partitioning the fragrance vinegar and chloroform using a separating funnel and recovering the chloroform phase. In this case, the partition is preferably carried out several times. The amount of chloroform added is preferably on the order of 10% by weight to 1000% by weight of the aqueous phase (fragrance vinegar), most preferably on the order of half to twice the amount of the aqueous phase. From the recovered chloroform phase, the solvent can be easily removed by concentration treatment or the like under reduced pressure. The solid or concentrated chloroform extract of the fragrance vinegar can be obtained.

Next, the fractionation step S3 by normal-phase chromatography shown in FIG. 1 will be described. This fractionation step S3 is aimed at purifying and separating the butenolide compound as the component of interest contained in the solvent extract obtained in the step S2. A fractionation treatment by normal-phase silica gel column chromatography will be described as one example. Specifically, this treatment is carried out, but not particularly limited to, by placing a silica gel with the solvent extract adsorbed thereon in a chromatographic column packed with a silica gel, and injecting a predetermined mobile phase thereon for elution. The mobile phase is not particularly limited, and benzene-acetone is preferably used. For example, the component of interest can be preferably separated by elution in a mobile phase having a gradient with benzene:acetone ratios of 40:1 to 0:1. Of the obtained fractions, a fraction containing the substance of interest can be confirmed by a PPARγ activation test, a test of measuring the expression level of a gene in which PPARγ is involved (UCP-1 gene, etc.), or the like as mentioned later.

Next, the fractionation step S4 by reverse-phase chromatography shown in FIG. 1 will be described. This fractionation step S4 is aimed at further purifying and separating the butenolide compound as the component of interest contained in the normal-phase column fraction obtained in the step S3 to substantially isolate the butenolide compound. A fractionation treatment by reverse-phase silica gel column chromatography will be described as one example. Specifically, this treatment is carried out, but not particularly limited to, by packing a column with a silica gel modified with an octadecylsilyl group ($C_{18}$), adding the fraction obtained in the step S3 to the column, and then injecting a predetermined mobile phase thereon for elution. The mobile phase is not particularly limited, and methanol-water is preferably used. For example, the component of interest can be preferably isolated by elution in a mobile phase having a gradient with methanol:water ratios of 1:9 to 1:0. Of the obtained fractions, a traction containing the butenolide compound, which is the substance of interest, can be confirmed by a PPARγ activation test, a test of measuring the expression level of a gene in which PPARγ is involved (UCP-1 gene, etc.), or the like as mentioned later. The obtained fraction is subjected to HPLC analysis, and the obtainment of a single peak can be confirmed by checking the chromatogram to confirm whether or not the butenolide compound can be isolated.

The aforementioned fractionation treatment S3 or S4 is not limited to a single treatment, and the fractionation treatment may be carried out several times using the same packing material or different packing materials or fractionation treatments in the same mobile phase or different mobile phases may be carried out in combination.

Alternatively, the butenolide compound represented by the formula (3) may be produced by a synthesis method known in the art, in addition to the method for obtaining the butenolide compound by extraction and separation from a fragrance vinegar. The butenolide compound of the present invention can be produced, for example, by aldol-condensing phenylacetaldehyde and glyoxylate ester to obtain 3-phenyl-4-oxo-2-hydroxy-butanoic acid ester, followed by the action of an acid in the presence of water (Japanese Patent Laid-Open No. 1994-211825) or by reacting phenylacetaldehyde with glyoxylate ester in the presence of morpholine hydrochloride (Japanese Patent Laid-Open No. 1999-152280). Likewise, other butenolide compounds represented by the formula (4) and the formula (1) can also be produced by synthesis methods known in the art (see e.g., J. Org. Chem., 1981, vol. 46, pp. 4889-4894; and Tetrahedron Letters, 2013, vol. 54, pp. 5322-5324).

The pharmaceutically acceptable salt of the aforementioned butenolide compound is not particularly limited and can be any salt formed with an acid or a base. This butenolide compound or the salt thereof may be a hydrate, an organic solvate such as an alcoholate or may be an anhydrate. The butenolide compound or the salt thereof also includes, for example, various isomers or racemates, or mixtures thereof. The butenolide compound or the salt thereof may be a prodrug that contains, for example, a modified functional group in the molecular structure and exhibits effects as a result of metabolism.

The butenolide compound represented by the formula (1) has the effect of activating PPARγ. In the present invention, the PPARγ activator refers to a substance that can adjust the expression of a target gene by activating PPARγ through binding or the like to the PPARγ. Examples of the target gene of PPARγ include genes of adiponectin, UCP-1, fatty acid-binding protein, and aP2. In the present specification, the PPARγ ligand activity is used interchangeably with PPARγ agonist activity.

The PPARγ activator of the present invention can be used in the treatment, prevention, inhibition, or amelioration of a pathological condition, a symptom, or a disease involving PPARγ. In this context, the treatment or the amelioration of the pathological condition also includes the prevention of the disease or the pathological condition, or catamnestic treatment. The disease involving PPARγ includes a wide range of diseases caused by the involvement thereof in the differentiation or metabolism of fat cells and particularly includes insulin resistance, diabetes mellitus, hyperlipidemia, hypertension, visceral fat obesity, visceral fat accumulation, subcutaneous fat accumulation, fatty liver, body weight gain, obesity, leptin resistance, arteriosclerosis, inflammatory diseases, malignant tumors, or metabolic syndrome, or diseases associated therewith. The PPARγ activator of the present invention is used in the treatment or amelioration of one or more of these diseases, the inhibition or prevention of their symptoms or pathological conditions, or the like.

The butenolide compound of the present invention also has the effect of converting white fat cells working to accumulate fat to brown fat cells working to burn fat and as such, can be used as a lipid metabolism activator. The mechanism of action as the lipid metabolism activator is not limited to the aforementioned conversion of white fat cells to brown fat cells and is also related to the PPARγ-activating effect of the compound of the present invention to enhance the transcription of the target gene of PPARγ.

The butenolide compound represented by the formula (1) further has a PPARγ-activating effect and as such, can be used as an antidiabetic agent, a therapeutic agent for insulin resistance, an anti-obesity agent, a body weight gain inhibitor, a visceral fat accumulation inhibitor, a subcutaneous fat accumulation inhibitor, a therapeutic agent for leptin resistance, a therapeutic agent for abnormal lipid metabolism, an antilipidemic agent, a therapeutic agent for arteriosclerosis, and a metabolic syndrome inhibitor.

The PPARγ activator, etc., of the present invention comprises the butenolide compound represented by the aforementioned formula (1) as an active ingredient and can be used as a pharmaceutical drug, a quasi drug, and a food for humans or animals. The food also includes supplements, health foods, functional foods, foods for specified health use, or the like.

In the case of using the PPARγ activator, etc., of the present invention as a pharmaceutical drug or a quasi drug, these drugs can be prepared in various forms by conventional methods routinely used. In this case, these drugs can be usually formulated using additives acceptable as pharmaceutical additives, such as a pharmaceutically acceptable carrier or excipient for preparations, a lubricant, a dispersant, a disintegrant, a buffer, a solvent, an expander, a preservative, a flavor, or a stabilizer. A drug delivery system including a formulation technique such as microcapsules, liposome preparations, pulverization, or clathration using cyclodextrin or the like can be further used in order to improve the bioavailability or stability of this butenolide compound.

In the case of using the PPARγ activator, etc., of the present invention as an oral administration preparation, this preparation can be used in the form of tablets, granules, capsules, or solutions for internal application and is preferably used in a form suitable absorption from the gastrointestinal tract. The conventional formulation technique can also be used for providing the preparation in a form desired for the reason of distributability, storage stability, etc. In the case of using the PPARγ activator, etc., of the present invention as a parenteral administration preparation such as a preparation for external use, this preparation can be used in the form of, for example, injections, suppositories, or transdermal absorption agents such as tapes or cataplasms. Alternatively, a solid preparation may be dissolved in an appropriate solvent before use and then used for the reason of distributability, storage stability, etc. Also, the conventional formulation technique may be used for providing the forms solutions and semisolid agents.

In the case of using the PPARγ activator, etc., of the present invention as a food, examples of the form thereof include: supplement forms such as tablets, capsules, granules, and syrups; and other forms such as soups, rice porridges, drinks, noodles, jellies, cereals, bread, dairy products, seasonings, edible oils, and confectionery. Alternatively, the PPARγ activator, etc., of the present invention may be used as a food for animals (feed, pet foods (dry type and wet type), supplements for animals, drinks for animals, etc.). For use as a food, the food may be supplemented with various components (e.g., extracts) derived from a fragrance vinegar, nutrients (e.g., vitamins, minerals, or amino acids), or the like.

The dose or effective intake of the PPARγ activator, etc., of the present invention varies depending on intended therapeutic effects, an administration method, a recipient, and a dosage form and therefore, is not particularly limited. The oral daily dose is approximately 0.01 µg/60 kg body weight to approximately 300 mg/60 kg body weight, preferably 0.05 µg/60 kg body weight to approximately 100 mg/60 kg body weight, of the active ingredient, which is preferably administered in one portion or three divided portions. Also, the parenteral daily dose is approximately 0.01 µg/60 kg body weight to 100 mg/60 kg body weight, preferably approximately 0.03 µg/60 kg body weight to 50 mg/60 kg body weight, of the active ingredient.

Next, the present invention will be described in more detail with reference to Examples. However, the present invention is not intended to be limited by these Examples by any means.

EXAMPLES

A measurement method for the PPAR activation test in Examples below were conducted as described below.
(1) PPARγ Activation Test
(1-1) Preparation
A plasmid pM-PPARγ for the expression of a chimeric protein composed of a human-derived PPARγ ligand-binding domain and a DNA-binding domain of a yeast-derived GAL4 transcription factor, and a plasmid p4×UASg-tk-luc containing a *Cypridina*-derived luciferase structural gene linked downstream of a GAL4 responsive sequence designed such that its expression was controlled by this chimeric protein, were prepared. Also, a *Renilla*-derived luciferase expression plasmid pRL-CMV having a viral expression promoter for constitutive intracellular expression was prepared as a plasmid for the correction of transfection efficiency. On the other hand, DMEM containing 10% FBS was used as a medium for CV-1 cells (African green monkey kidney-derived). The CV-1 cells were seeded at $4.5 \times 10^5$ cells over a 100-mm Petri dish and cultured in an incubator at 37° C. in a 5% $CO_2$ environment.
(1-2) Transformation of CV-1 Cell The CV-1 cells thus cultured for 24 hours were cotransfected with 2.0 µg of pM-PPARγ, 4.0 µg of p4×UASg-tk-luc, and 0.04 µg of pRL-CMV to transform the CV-1 cells. The transformation was carried out by the liposome method using LipofectAMINE(R) Reagent (a product of Invitrogen Corp.). After the transformation operation, the cells were cultured at 37° C. for 3.5 hours in a 5% $CO_2$ environment.
(1-3) Addition of Test Sample The CV-1 cells thus incubated were recovered by trypsin treatment, and 50 mL thereof was inoculated at a concentration of $1 \times 10^5$ cells/mL to a 96-well plate. Each test sample was diluted with DMEM containing 4% FBS to adjust its concentration to twice the final concentration, and 50 mL thereof was added to the 96-well plate mentioned above. DMSO was used as a control substance. After the addition of the test sample or the control substance (DMSO), the mixture was incubated at 37° C. for 24 hours in a 5% $CO_2$ environment.
(1-4) Measurement of Luciferase Activity The luciferase activity was measured using Dual-Luciferase(R) Reporter Assay System (a product of Promega K.K.). The culture solution was removed from the 96-well plate. The cells were washed with PBS(−), and moisture was removed therefrom using a paper towel. To the cells, 30 mL of a cell lysis solution (Passive Lysis Buffer) was added, and the 96-well plate was shaken for 15 minutes. The cell extract was transferred at 10 mL/well to a 96-well luminoplate. A luminescent substrate solution was added thereto at 70 mL/well. The luminescence intensity based on the luciferase was measured for a measurement time set to 10 seconds using a luminometer (Micro Lumat Plus, a product of Berthold Japan Co., Ltd.).

The PPARγ-activating effect of the test sample was evaluated on the basis of a ratio (%) relative to controls. In order to correct transfection efficiency, the measured *Cypridina* luciferase activity value (A) was divided by the measured *Renilla* luciferase activity value (B) to determine a value (A/B). The average A/B value of the control group was calculated and defined as 100. The A/B value of the test sample was calculated, and the ratio (%) of this value to the average value of the controls was used as the ability of the test sample to activate PPARγ.

Example 1

Preparation and Activity Measurement of Normal-phase Column Fraction

According to the fractionation flow shown in FIG. 2, 7 normal-phase column fractions were prepared from fragrance vinegar. Hereinafter, each treatment in the fractionation flow will be described in detail.
(1) Delipidation Treatment by Hexane
To 1 L of a fragrance vinegar (product name: KOJUN KOZU Aged 8 Years, a product of Kojun Japan Co., Ltd.), an equal amount of n-hexane was added, and the mixture was well stirred and then centrifuged at 5000 rpm for 10 minutes to recover an aqueous layer. This partition operation was carried out 3 times to remove redundant lipid components contained in the fragrance vinegar.

(2) Extraction Treatment by Chloroform

Next, to the recovered aqueous layer, an equal amount of chloroform was added. Partition operation was carried out 3 times using a separating funnel to recover a chloroform layer. The recovered chloroform layer was concentrated under reduced pressure for the removal of the solvent to obtain 3970 mg of a chloroform extract.

(3) Normal-phase Silica Gel Column Treatment

The extract (3970 mg) obtained by the chloroform extraction was dissolved in a small amount of acetone and adsorbed onto 130 g of a silica gel (Silica Gel 60, for 0.040-0.063 mm column chromatography; a product of Merck Millipore). Next, a chromatographic glass column (chromatographic column length: 60 cm, diameter: 2.7 cm, volume: 343 mL) was packed with 130 g of a silica gel, on which the silica gel with the chloroform extract of the fragrance vinegar adsorbed thereon was then placed. Solvents (550 mL each) were injected in the order of benzene:acetone=20:1, 10:1, 5:1, 3:1, 2:1, and 1:1 and 100% acetone. The eluted fractions were divided on a solvent basis and recovered as normal-phase column fractions (Fr. 1 to 7). The recovered fractions were each concentrated under reduced pressure for the removal of the solvents, and the solid weights of the resulting fractions were measured. A portion of each obtained fraction was dissolved in an appropriate amount of dimethyl sulfoxide (DMSO, a product of Nacalai Tesque, Inc.) to adjust its concentration to 1000 or more times the final concentration for the PPARγ ligand activity measurement.

(4) Activity Measurement of Normal-phase Column Fraction

The 7 normal-phase column fractions obtained in Example 1 were subjected as test samples to the PPARγ activation test to evaluate the PPARγ ligand activity of each fraction. The final concentrations of each fraction were set to 100 μg/mL and 50 μg/mL. The PPARγ ligand activity of each fraction is shown in FIG. 3. The ordinate of the drawing depicts the ratio of the activity of the fraction to the activity of the control substance (DMSO). As shown in FIG. 3, the fraction of Fr. 1 (elution solvent: benzene:acetone=20:1) was confirmed to have PPARγ ligand activity in a concentration-dependent manner.

Example 2

Preparation and Activity Measurement of Reverse-phase Column Fraction (1) Reverse-phase ODS Column Treatment According to the fractionation flow of FIG. 4, the normal-phase column fraction of Fr. 1 obtained and confirmed to have PPARγ-activating effect in Example 1 was further subjected to reverse-phase chromatography to prepare 5 reverse-phase column fractions. The reverse-phase chromatography was carried out as follows: a chromatographic glass column (chromatographic column length: 40 cm, diameter: 2.2 cm, volume: 152 mL) was packed with 50 g of an ODS silica gel (YMC*GEL ODS-A 6 nm S-150 μm; a product of YMC Co., Ltd.) as a packing material suspended in methanol. To this packing material, 100 mL of 100% degassed methanol was poured and injected so as to prevent foaming. Next, the packing material was equilibrated with an aqueous solution of 10% degassed methanol in an amount of 10 times (760 mL) the amount of the packing material. The fraction of Fr. 1 (117 mg) obtained in Example 1 was dissolved in methanol, and the solution was added into the packing material. Then, aqueous solutions of degassed methanol having a methanol concentration of 10%, 20%, 30%, 40%, and 100% were injected (180 mL each) onto the packing material in the order of the presented concentrations. The eluted fractions were divided on a solvent basis and recovered as reverse-phase column fractions (Fr. 1 to 5). The obtained reverse-phase column fractions were each concentrated under reduced pressure for the removal of the solvents. A portion of each obtained fraction was dissolved in an appropriate amount of dimethyl sulfoxide. The separation statuses of the recovered fractions were confirmed by use of high-performance liquid chromatography (column used: YMC-Pack ODS-A 250×4.6 mm I.D. S-5 μm 30 nm, mobile phase: 20% aqueous methanol solution-70% aqueous methanol solution, flow rate: 1 mL/min, column temperature: 40° C., detection conditions: UV 280 nm). The results of HPLC on each fraction are shown in FIG. 5. The abscissa of FIG. 5 depicts retention time (min).

(2) Activity Measurement of Reverse-phase Column Fraction

The reverse-phase column fractions (Fr. 1 to 5) obtained in Example 2 and the normal-phase column fraction of Fr. 1 obtained in Example 1 were subjected as test samples to the PPARγ activation test to evaluate the PPARγ ligand activity of each fraction. The final concentration of each fraction was set to 100 μg/mL. In addition, the PPARγ activation test was also conducted on a PPARγ agonist troglitazone (Tro). The final concentration of troglitazone was set to 1 μM. The PPARγ ligand activity is shown in FIG. 6. The ordinate of the drawing depicts the ratio of the activity of the fraction to the activity of the control substance (DMSO). As shown in FIG. 6, the reverse-phase column fractions of Fr. 4 (elution solvent: water:methanol=60:40) and Fr. 5 (elution solvent: 100% methanol) were confirmed to have PPARγ ligand activity.

Example 3

Preparation and Activity Measurement of Peak Fraction (1) Fractionation by High-performance Liquid Chromatography Referring to the HPLC chromatogram of the reverse-phase column fractions shown in FIG. 5, a plurality of specific peaks are found in the fractions of Fr. 4 and 5 confirmed to have a PPARγ-activating effect. Thus, an attempt was made to purify active substances by fractionating the fractions of Fr. 4 and 5 as to substances exhibiting the specific peaks. The fractionation was carried out by use of reverse-phase high-performance liquid chromatography (column used: YMC-Pack ODS-A 250×4.6 mm I.D. S-5 μm 30 nm, mobile phase: 20% aqueous methanol solution-70% aqueous methanol solution, flow rate: 1 mL/min, column temperature: 40° C., detection conditions: UV 280 nm).

(2) Activity Measurement of Peak Fraction

The peak fractions obtained in Example 3 and troglitazone (Tro) were subjected as test samples to the PPARγ activation test to evaluate the PPARγ ligand activity of each fraction. The final concentration of each fraction was set to 100 μg/mL, and the final concentration of troglitazone was set to 1 μM. The results are shown in FIG. 7. As shown in FIG. 7, the fraction of peak 5 of Fr. 4 was confirmed to have distinct PPARγ ligand activity. As a result of HPLC analysis, this fraction of peak 5 was detected as a single peak (see FIG. 8), demonstrating that the active substance was able to be isolated as a single component.

The fraction of peak 5 obtained in Example 3, the reverse-phase column fraction of Fr. 5 obtained in Example 2, and troglitazone were further subjected to the PPARγ activation test to evaluate the PPARγ ligand activity of each fraction. The final concentrations of the fraction of peak 5 were set to 50 μg/mL as a low concentration and 100 μg/mL as a high concentration; the final concentrations of the reverse-phase column fraction of Fr. 5 were set to 25 μg/mL and 50 μg/mL; and the final concentration of troglitazone was set to 10 μM. The results are shown in FIG. 9. As shown in FIG. 9, the PPARγ ligand activity of the fraction of peak 5 was confirmed to elevate in a concentration-dependent manner.

Example 4

Structural Determination of Peak Fraction

The fraction of peak 5 obtained in Example 3 was structurally analyzed. The structural analysis was conducted by LC/MS, $^1$H-NMR, $^{13}$C-NMR, HMBC, and HSQC. The results of LC/MS are shown in FIG. 10. The abscissa of FIG. 10 depicts m/z values. The ordinate thereof depicts detection intensity. FIG. 10 suggested that the fraction of peak 5 has a molecular weight of 176.1687 and a rational formula $C_{10}H_8O_3$. The results of $^1$H-NMR, $^{13}$C-NMR, HMBC, and HSQC demonstrated that the component contained in peak 5 was 5-hydroxy-4-phenylbutenolide (hereinafter, referred to as "5H4PB").

Example 5

Measurement of UCP-1 Gene Expression Level

Mitochondrial uncoupling proteins (or uncoupling proteins: UCPs) have the function of uncoupling oxidative phosphorylation reaction in the mitochondrial inner membrane to consume the energy as heat. Among them, UCP-1 is specifically expressed in brown fat cells that produce heat by burning fat. In recent years, particular synthetic PPARγ agonists have been reported to convert white fat cells working to store fat to brown fat cells working to burn fat (H. Ohno et al, Cell metabolism, 2012, Vol. 15, pp. 395-404). Thus, the test of measuring the expression level of the UCP-1 gene was conducted in order to confirm whether the fraction of peak 5 confirmed to have PPARγ ligand activity, i.e., 5H4PB, had the effect of converting white fat cells to brown fat cells.

The test was conducted as follows: a mesenchymal cell line 10T1/2 was inoculated at 1×10$^4$ cells/mL to a 12-well plate. The cells were cultured until confluent. Then, the fraction of peak 5 (5H4PB) was added thereto such that its final concentration was 100 μg/mL. DMSO was used as a control substance. Twenty-four hours after the sample addition, mRNA was recovered from the cells, and the mRNA level was determined. The mRNA quantification was carried out using LightCycler(R) (Roche Applied Science). The results are shown in FIG. 11. The ordinate of the drawing depicts the ratio of the UCP-1 expression level for the fraction of peak 5 to the UCP-1 expression level for the control substance (DMSO). As shown in FIG. 11, the fraction of peak 5 was found to have the effect of elevating the expression level of UCP-1. The increased expression level of UCP-1 indicates enhanced heat production from lipids. These results demonstrated that the fraction of peak 5, i.e., 5H4PB, contributes to the amelioration and promotion of lipid metabolism via the activation of UCP-1.

Example 6

Synthesis of 5H4PB

5H4PB was synthesized in order to confirm whether 5H4PB obtained by chemical synthesis had a PPARγ-activating effect similar to that of 5H4PB obtained by extraction from the fragrance vinegar. The synthesis was carried out as follows: 100 mg of glyoxylic acid monohydrate and 150 mg of morpholine were dispersed in 450 μL of 1,4-dioxane. To the dispersion, 55 μL of water was added dropwise. To the mixture, 140 mg of phenylacetaldehyde was added, and the mixture was left standing at room temperature for 1 hour and then heated to reflux for 24 hours. The resulting product was concentrated under reduced pressure, followed by extraction with 2.5 mL of diethyl ether. The extracted diethyl ether layer was dehydrated and dried by the addition of anhydrous magnesium sulfate and then concentrated again under reduced pressure. The concentrate was dissolved in an acetone/chloroform mixed solution and recrystallized to obtain 140 mg of 5H4PB. The 5H4PB thus synthesized was subjected to liquid chromatography/mass spectrometry (LC/MS) to confirm that this compound was identical to the 5H4PB obtained by extraction from the fragrance vinegar (fraction of peak 5 obtained in Example 3).

Example 7

Activity Measurement of Synthesized Product

The synthesized 5H4PB obtained in Example 6 was subjected as a test sample to the PPARγ activation test. The final concentration of the synthesized 5H4PB was set to 3.5 μM. The results are shown in FIG. 12. The ordinate of the drawing depicts the ratio of the activity of the synthesized product to the activity of the control substance (DMSO). As shown in FIG. 12, the 5H4PB obtained by chemical synthesis was also confirmed to have high PPARγ ligand activity, as with the fragrance vinegar-derived one.

Example 8

Synthesis of Various Butenolide Compounds and Activity Measurement of each Synthesized Product Various butenolide compounds including 5H4PB were chemically synthesized, and their PPARγ ligand activity was measured at varying concentrations. In this Example, the synthesis of 5H4PB and various butenolides was carried out as follows: for 5H4PB represented by the formula (3), first, 53 mL (0.6 mol) of morpholine and 120 mL of 1,4-dioxane were sequentially added to a 1-L four-neck flask. While the flask was placed in an ice bath, 62 mL (0.6 mol, 1.5 equivalents) of a 50% aqueous glyoxylic acid solution and 50 mL of concentrated hydrochloric acid were sequentially added dropwise thereto. This mixture was heated to an internal temperature of 87° C. Phenylacetaldehyde (48% solution in diethyl phthalate, 0.4 mol) diluted 3-fold with 1,4-dioxane was gradually added dropwise thereto, and this mixed solution was refluxed overnight. The reaction solution thus refluxed was confirmed by use of thin-layer chromatography to be free from aldehyde. The reaction solution was allowed to cool to room temperature. The reaction solution was concentrated, and 200 mL of ethyl acetate was added thereto. After washing with a saturated aqueous solution of sodium bicarbonate, the resulting organic layer was dried over sodium sulfate, filtered, and concentrated to obtain 101 g of a yellow solid partially containing an oil. This yellow solid was dissolved by the addition of 200 mL of ethyl acetate. To the solution, alumina (basic) was added, and the mixture was stirred and subjected to batch treatment. The alumina was filtered off, and the filtrate was then concentrated to obtain 96 g of a yellow solid (partially containing an oil). This solid was dissolved in a 0.5-fold amount of ethyl acetate. To the solution, a 1-fold amount of hexane was added, and the mixture was stirred. The deposited solid was collected by filtration to obtain 30.2 g of a milky white solid 5H4PB (yield: 40%, GC purity: 98.6%).

Also, 5-hydroxy-4-(4-methylphenyl)butenolide represented by the formula (4) ($R^2$ in the formula (1): a methylphenyl group) was chemically synthesized in the same way as the method for synthesizing 5H4PB of this Example (molar ratio of each reagent, reaction time, etc.) except that: 4-methylphenylacetaldehyde (48% solution in diethyl phthalate, 0.4 mol) was used instead of phenylacetaldehyde; the dropwise addition temperature of this aldehyde was set to an internal temperature 60° C. of the mixture; and after the completion of the dropwise addition, the reaction solution was heated to an internal temperature of 87° C. The obtained compound had a yield of 30% and a GC purity of 97.6%.

As for the chemical synthesis of 5-hydroxy-4-(4-methylbenzyl)butenolide represented by the formula (5) give below ($R^2$ in the formula (1): a methylbenzyl group), the mixed solution was reacted by overnight reflux in the same way as the aforementioned method for synthesizing 5H4PB except that 3-(4-methylphenyl)propionaldehyde (48% solution in diethyl phthalate, 0.4 mol) was used instead of phenylacetaldehyde. The reaction solution thus refluxed was confirmed by use of thin-layer chromatography to be free from aldehyde. The reaction solution was allowed to cool to room temperature. The reaction solution was concentrated, and a 2-fold amount of ethyl acetate was added thereto. This solution was washed with dilute hydrochloric acid and a saturated aqueous solution of sodium bicarbonate to remove components difficult to fractionate with columns. The obtained organic layer was dried over sodium sulfate, filtered, and concentrated to obtain a crude solid. This solid was dissolved in a 10-fold amount of a mixed solvent of hexane/ethyl acetate=1 and subjected to batch treatment using a 3-fold amount of silica gel (PQS100B). To the obtained concentrate, hexane was added, and the deposited solid was collected by filtration to obtain a colorless solid 5-hydroxy-4-(4-methylbenzyl)butenolide at a yield of 24% and a GC purity of 99.2%.

[Formula 5]

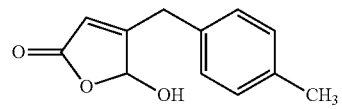

(5)

As for the chemical synthesis of 5-hydroxy-4-benzylbutenolide represented by the formula (6) give below ($R^2$ in the formula (1): a benzyl group), the mixed solution was reacted by overnight reflux in the same way as the aforementioned method for synthesizing 5H4PB except that 3-phenylpropionaldehyde (48% solution in diethyl phthalate, 0.4 mol) was used instead of phenylacetaldehyde. The reaction solution thus refluxed was confirmed by use of thin-layer chromatography to be free from aldehyde. The reaction solution was allowed to cool to room temperature. The reaction solution was concentrated, and a 2-fold amount of ethyl acetate was added thereto. After washing with a saturated aqueous solution of sodium bicarbonate, the resulting organic layer was dried over sodium sulfate, filtered, and concentrated to obtain a crude solid. This crude solid was purified using a silica gel (PQS100B, developing solvent: hexane/ethyl acetate=4→2.3). To the obtained concentrate, hexane was added, and the deposited solid was collected by filtration to obtain a colorless solid 5-hydroxy-4-benzylbutenolide at a yield of 60% and a GC purity of 99.6%.

[Formula 6]

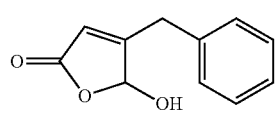

(6)

The 4 butenolide compounds thus synthesized, i.e., 5H4PB ($R^2$ in the formula (1): a phenyl group), 5-hydroxy-4-(4-methylphenyl)butenolide ($R^2$ in the formula (1): a methylphenyl group), 5-hydroxy-4-benzylbutenolide ($R^2$ in the formula (1): a benzyl group), and 5-hydroxy-4-(4-methylbenzyl)butenolide ($R^2$ in the formula (1): a methylbenzyl group), were tested at the test sample concentrations shown in Table 1 below. Their PPARγ ligand activity was measured in the same way as in Example 7 except that the incubation time after the test sample addition was set to 48 hours. The results are shown in Table 1 below and FIG. 13. The values shown in the table below and the ordinate of the drawing depict the ratio (%) of the activity of each synthesized product to the activity of the control substance (DMSO). In Table 1 and FIG. 13, these various butenolide compounds used as test samples were each indicated by the functional group of $R^2$ in the formula (1).

TABLE 1

|  |  | Test sample concentration (µg/mL) | | | | | | | | |
| --- | --- | --- | --- | --- | --- | --- | --- | --- | --- | --- |
|  |  | 0.032 | 0.08 | 0.16 | 0.4 | 0.8 | 2 | 4 | 10 | 20 |
| R2 in formula 1 | Phenyl (5H4PB) | 100 | 80 | 120 | 120 | 220* | 370* | 520* | 710* | — |
|  | Methylphenyl | 170 | 110 | 120 | 180 | 260* | 560* | 710* | 1270* | — |
|  | Benzyl | 120 | 220 | 110 | 130 | 170 | 310* | 360* | — | — |
|  | Methylbenzyl | 130 | 110 | 120 | 130 | 140 | 130 | 240* | 340* | 520* |

As shown in Table 1 and FIG. 13, all of the 4 test samples were found to have PPARγ ligand activity. Among them, a test area having a numeric value with the mark * in Table 1 indicates twice or more activity as compared with the control with p<0.05 (significantly different). These results demonstrated that: 5H4PB ($R^2$: a phenyl group) and 5-hydroxy-4-(4-methylphenyl)butenolide ($R^2$: a methylphenyl group) exhibit high activity in the range of 0.8 to 10 μg/mL; 5-hydroxy-4-benzylbutenolide ($R^2$: a benzyl group) exhibits high activity in the range of 2 to 4 μg/mL; and 5-hydroxy-4-(4-methylbenzyl)butenolide ($R^2$: a methylbenzyl group) exhibits high activity in the range of 4 to 20 μg/mL. Among them, 5H4PB and 5-hydroxy-4-(4-methylphenyl)butenolide were shown to have high activity in a low concentration range, and, particularly, 5-hydroxy-4-(4-methylphenyl) butenolide was shown to have the highest activity.

Example 9

Verification of Anti-obesity Effect on Dietary-induced Obesity Mouse Model

The 5H4PB obtained in Example 6 administered to mice fed with a high-fat diet to verify its anti-obesity effect. Five-week-old male C57BL/6J mice (supplied by Charles River Laboratories Japan, Inc.) were individually raised (one per cage) under environmental conditions involving a temperature of 20 to 26° C., a humidity of 35 to 75%, and 12-hour illumination (7:00 to 19:00). After acclimatization for approximately 1 week, the mice were divided into 6 groups each involving 6 to 8 individuals. Of the test groups, a normal group was fed with a normal solid diet CRF1 (a product of Oriental Yeast Co., Ltd., 3.57 kcal/g) during the test period, and a control group and drug administration groups were fed with a high-calorie solid diet D12492 (a product of Research Diets, Inc., 5.24 kcal/g) during the test period. The diets were freely taken, and water was also freely taken from water supply bottles.

TABLE 2

| NO. | Test group | Dose of drug | Feeding | The number of individuals |
|---|---|---|---|---|
| 1 | Normal | — | Normal diet CRF1 (3.57 kcal/g) | 6 |
| 2 | Control | — | High-fat diet D12492 (5.24 kcal/g) | 8 |
| 3 | 5H4PB | 0.037 μg/kg/day | | 8 |
| 4 | | 0.01 mg/kg/day | | 8 |
| 5 | Rosiglitazone | 0.037 μg/kg/day | | 6 |
| 6 | (positive control) | 10 mg/kg/day | | 6 |

The test substance 5H4PB (produced in Example 6) or a positive control substance rosiglitzaone (a product of Wako Pure Chemical Industries, Ltd.) was administered once a day for 12 weeks at the predetermined dose shown in Table 2 to the mice in each drug administration group. The rosiglitazone is a selective PPARγ ligand and is a substance having the effect of lowering the concentrations of glucose, fatty acid, and insulin in blood through binding to PPARγ. For the administration, body weight measurement was carried out once a week to calculate the dose to each individual. 5H4PB and rosiglitazone were each suspended in a 0.5 w/v % aqueous methylcellulose solution and diluted with the same aqueous solution to adjust the administration dose to 10 mL/kg. Then, each substance was forced-administered into the stomach using a syringe and a flexible stomach tube. A 0.5 w/v % aqueous methylcellulose solution was administered alone once a day for 12 weeks at a dose of 10 mL/kg to the mice in the normal group and the control group.

From the start of the test (administration), the body weight of each individual was measured at a frequency of once a week, and the average body weight of each test group was determined. The results are shown in FIG. 14. The ordinate of the drawing depicts mouse body weight (g). The abscissa thereof depicts the number of days (d) from the start of the test. As shown in FIG. 14, the control group was confirmed to have significant increase in body weight as compared with the normal group at 21 days into the test or later. The inhibition of body weight gain attributed to the high-calorie diet was shown in the groups given 5H4PB compared with the control group. Specifically, the body weight gain was inhibited by 25.8% in the test group given 0.037 μg/kg/day of 5H4PB and inhibited by 27.8% In the test group given 0.01 mg/kg/day of 5H4PB, with respect to the amount of body weight gain of the control group attributed to the high-calorie diet (the value determined by subtracting the body weight of the normal group from the body weight of the control group) at the completion of the test (84th day). Thus, 5H4PB was confirmed to have a high anti-obesity effect. On the other hand, according to the results of administering rosigilitazone having PPARγ ligand activity, the body weight of the low-dose test group given 0.037 μg/kg/day of rosigilitazone was increased more than the control group, and no anti-obesity effect was observed therein. Also, the high-dose test group given 10 mg/kg/day of rosiglitazone exhibited a lower rate of body weight gain inhibition even as compared with the test group given 0.037 μg/kg/day of 5H4PB. These results demonstrated that 5H4PB produces an anti-obesity effect even when administered at a low dose.

Example 10

Measurement of Adiponectin in Blood of Dietary-induced Obesity Mouse Model

Adiponectin is a secretory protein related to dysmetabolic syndrome such as insulin resistance, diabetes mellitus or arteriosclerosis. Adiponectin-deficient mice have the properties of being more likely to develop insulin resistance and being more likely to be affected by arteriosclerosis than wild-type mice. In humans as well, it is known that lowered adiponectin concentrations are related to dysmetabolic syndrome such as diabetes mellitus and arteriosclerosis. Thus, the dietary-induced obesity mouse models of Example 9 were subjected to the test of measuring the amount of adiponectin in blood.

For each individual of the male C57BL/6J mice after a lapse of 85 days into the test of Example 9, blood was collected from the abdominal vena cava using a syringe supplemented with heparin under anesthesia with 2% isoflurane. The amount of blood collected was set to approximately 0.8 mL. The collected blood was stored under ice cooling until centrifugation. After centrifugation (conditions: 4° C., approximately 1800×g, 10 min), the upper layer was recovered to obtain plasma. The plasma was dispensed to sampling tubes and cryopreserved until measurement. The mouse adiponectin concentration contained in the mouse plasma obtained from each individual was measured using a commercially available ELISA kit, and the average adiponectin concentration of each test group was determined. The results are shown in FIG. 15.

The ordinate of the drawing depicts the concentration (ng/mL) of adiponectin in the mouse plasma. Each bar of the bar graph represents the normal group, the control group, the 5H4PB 0.037 µg/kg/day administration group, the 5H4PB 0.01 mg/kg/day administration group, the rosiglitazone 0.037 µg/kg/day administration group, and the rosiglitazone 10 mg/kg/day administration group from the left to the right. From these results, the adiponectin concentration was confirmed to elevate in the 5H4PB administration groups compared with the control group. As a result of the t test, a significant rise in adiponectin concentration was confirmed, particularly, in the 0.01 mg/kg/day administration group. These results demonstrated that the administration of 5H4PB brings about preventive and ameliorating effects on insulin resistance, diabetes mellitus, hyperlipidemia, arteriosclerosis, or the like placed under the action of adiponectin.

Example 11

Measurement of Insulin in Blood of Dietary-induced Obesity Mouse Model

In Example 10, the amount of moose insulin contained in the mouse plasma obtained from each individual was measured using a commercially available ELISA kit, and the average insulin concentration of each test group was determined. The results are shown in FIG. 16. The ordinate of the drawing depicts the insulin concentration (ng/mL) in the mouse plasma. The test group indicated by each bar of the bar graph is the same as in FIG. 15 mentioned above. From these results, the inhibition of a rise in insulin concentration was confirmed in the 5H4PB administration groups, particularly, the low-dose group, compared with the control group having hyperinsulinemia caused by obesity. These results demonstrated that the administration of 5H4PB brings about preventive and ameliorating effects on insulin resistance or diabetes mellitus.

Example 12

Measurement of Leptin in Blood of Dietary-induced Obesity Mouse Model

Leptin is a protein hormone that regulates appetite and metabolism. The leptin concentration in blood is known to elevate due to obesity, resulting in leptin resistance. In Example 10, the amount of mouse leptin contained in the mouse plasma obtained from each individual was measured using a commercially available ELISA kit, and the average leptin concentration of each test group was determined. The results are shown in FIG. 17. The ordinate of the drawing depicts the leptin concentration (pg/mL) in the mouse plasma. The test group indicated by each bar of the bar graph is the same as in FIGS. 15 and 16 mentioned above. From these results, the inhibition of a rise in leptin concentration was confirmed in a dose-dependent manner in the 5H4PB administration groups compared with the control group having hyperleptinemia caused by obesity. These results demonstrated that the administration of 5H4PB brings about preventive and ameliorating effects on leptin resistance or obesity.

Example 13

Measurement of Amounts of Subcutaneous Fat and Visceral Fat in Dietary-induced Obesity Mouse Model For each individual of the male C57BL/6J mice after lapse of 85 days into the test of Example 9, blood was collected under anesthesia with 2% isoflurane, and the mice were then euthanized. Inguinal subcutaneous fat, epididymal fat, perirenal fat, and mesenteric fat were collected from each individual. The weight of each fat was measured, and the average fat weights of each test group were determined.

The results are shown in FIGS. 18(A) to 18(D). The ordinate of the drawing depicts the measured weight (g) of each fat tissue. Each bar of the bar graph indicates the normal group, the control group, the 5H4PB 0.037 µg/kg/day administration group, the 5H4PB 0.01 mg/kg/day administration group, the rosiglitazone 0.037 µg/kg/day administration group, and the rosiglitazone 10 mg/kg/day administration group from the left to the right. As shown in FIG. 18, these results demonstrated that the accumulation of subcutaneous fat and visceral fat due to the high-calorie diet is inhibited in the 5H4PB administration groups compared with the control group. Specifically, increase in the amount of each fat tissue was inhibited by approximately 35% for the inguinal subcutaneous fat, approximately 18% for the epididymal fat, approximately 13% for the perirenal fat, and approximately 16% for the mesenteric fat in the test group administered 0.037 µg/kg/day of 5H4PB, while increase in the amount of each fat tissue was inhibited by approximately 34% for the inguinal subcutaneous fat, approximately 15% for the epididymal fat, approximately 13% for the perirenal fat, and approximately 40% for the mesenteric fat in the test group administered 0.01 µg/kg/day of 5H4PB, with respect to the amount of each fat tissue increased in the control group due to the high-calorie diet (the value determined by subtracting the fat tissue weight of the normal group from the fat tissue weight of the control group). Thus, 5H4PB administered at a low dose was confirmed to have subcutaneous fat and visceral fat accumulation inhibitory effects. According to the results of administering rosiglitazone having PPARγ ligand activity, the amount of visceral fat of the test group given the low dose (0.037 µg/kg/day) of rosiglitazone was increased more than the control group, and no visceral fat accumulation inhibitory effect was observed therein. These results demonstrated that 5H4PB produces subcutaneous fat and visceral fat accumulation inhibitory effects even when administered at a low dose.

Example 14

Study on Influence of Administration of 5H4PB on Liver Tissue

In Example 13, the liver was collected during the collection of fat tissues from each individual and histopathologically examined. The findings from the histopathological examination were as described below.

For the individuals of the normal group, the deposition of fat droplets was not observed in the hepatocytes, whereas only the very mild infiltration of inflammatory cells was observed. On the other hand, for the individuals of the control group, the very mild to mild depositions of small and large fat droplets were observed in the hepatocytes of 7 out of the 8 individuals, and the very mild infiltration of inflammatory cells was observed, as with the normal group. In the test group given 0.037 µg/kg/day of 5H4PB and the test group given 0.01 mg/kg/day thereof, no or only weak depositions of fat droplets were observed in the hepatocytes. In the rosiglitazone 0.037 µg/kg/day administration group, fine, small, and large fat droplets coexisted with each other in the hepatocytes, and the very mild to mild depositions thereof were observed. In the rosiglitazone 10 mg/kg/day administration group, these fat droplets were increased, and the moderate deposition thereof was observed while the hepatocytes were mildly swollen.

From these findings of the histopathological examination, 5H4PB was confirmed to be free from hepatic damage, as compared with the rosiglitazone administration groups or the control group. These results demonstrated that 5H4PB is a highly safe component.

Examples of the present invention mentioned above are to be considered in all respects as illustrative and no restrictive. Other various changes and modifications can be made in the embodiments of the present invention. Thus, the scope of the present invention is indicated by the appended claims and within the meaning and range of equivalency of the claims.

INDUSTRIAL APPLICABILITY

The present invention provides a PPARγ activator that prevents or ameliorates lifestyle-related diseases and other pathological conditions involving PPARγ and as such, is industrially useful in a wide range of fields of medicines and foods (also including supplements, health foods, functional foods, foods for specified health use, etc.).

The invention claimed is:

1. A method of treating, preventing, inhibiting or ameliorating a pathological condition, a symptom, or a disease involving PPARγ, comprising:
   administering a therapeutically effective amount of a butenolide compound represented by the formula (2) or a pharmaceutically acceptable salt thereof to the patient:

[Formula 2]

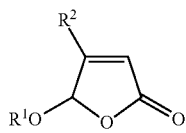

(2)

wherein $R^1$ represents a hydrogen atom, a phosphate group, a fatty acid group, an alkyl group having 1 to 4 carbon atoms and optionally having a substituent, or a sugar residue optionally having a substituent, and $R^2$ represents a phenyl group, a methylphenyl group, a dimethylphmyl group, an ethylphenyl group, a benzyl group, a methylbenzyl group, a dimethylbenzyi group, an ethylbenzyl group, a phenethyl group, a methylphenethyl group, a dimethylphenethyl group, or an ethylphenethyl group.

2. The method according to claim 1, wherein the pathological condition, the symptom, or the disease involving PPARγ is one or mare pathological conditions, symptoms, or diseases selected from the group consisting of diabetes mellitus, insulin resistance, obesity, body weight gain, visceral fat accumulation, subcutaneous fat accumulation, leptin resistance, abnormal lipid metabolism, hyperlipidemia, arteriosclerosis, and metabolic syndrome.

3. A method of treating obesity, comprising:
   administering a therapeutically effective amount of a compound represented by formula (3) or a pharmaceutically acceptable salt thereof to the patient:

[Formula 3]

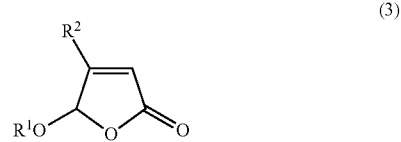

(3)

wherein $R^1$ represents a hydrogen atom, a phosphate group, a fatty acid group, an alkyl group having 1 to 4 carbon atoms and optionally having a substituent, or a sugar residue optionally having a substituent, and $R^2$ represents a phenyl group, a methylphenyl group, a dimethylphenyl group, an ethylphenyl group, a benzyl group, a methylbenzyl group, a dimethylbenzyl group, an ethylbenzyl group, a phenethyl group, a methylphenethyl group, a dimethylphenethyl group, or an ethylphenethyl group.

4. A method for inhibiting fat accumulation, comprising:
   administering a therapeutically effective amount of a compound represented by formula (4) or a pharmaceutically acceptable salt thereof to the patient:

[Formula 4]

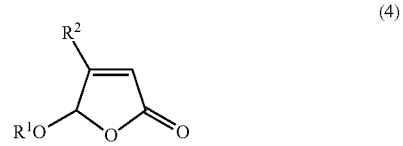

(4)

wherein $R^1$ represents a hydrogen atom, a phosphate group, a fatty acid group, an alkyl group having 1 to 4 carbon atoms and optionally having a substituent, or a sugar residue optionally having a substituent, and $R^2$ represents a phenyl group, a methylphenyl group, a dimethylphenyl group, an ethylphenyl group, a benzyl group, a methylbenzyl group, a dimethylbenzyl group, an ethylbenzyl group, a phenethyl group, a methylphenethyl group, a dimethylphenethyl group, or an ethylphenethyl group.

5. A method of treating diabetes mellitus or insulin resistance, comprising:
   administering a therapeutically effective amount of a compound represented by formula (5) or, a pharmaceutically acceptable salt thereof to the patient:

[Formula 5]

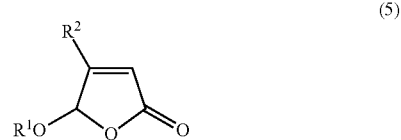

(5)

wherein $R^1$ represents a hydrogen atom, a phosphate group, a fatty acid group, an alkyl group having 1 to 4 carbon atoms and optionally having a substituent, or a sugar residue optionally having a substituent, and $R^2$ represents a phenyl group, a methylphenyl group, a dimethylphenyl group, an ethylphenyl group, a benzyl group, a methylbenzyl group, a dimethylbenzyl group, an ethylbenzyl group, a phenethyl group, a methylphenethyl group, a dimethylphenethyl group, or an ethylphenethyl group.

* * * * *